(12) United States Patent
Knuebel et al.

(10) Patent No.: US 7,135,047 B2
(45) Date of Patent: Nov. 14, 2006

(54) M-PHENYLENEDIAMINE DERIVATIVES AS COUPLER COMPONENTS FOR THE COLORING OF KERATINIC FIBERS

(75) Inventors: Georg Knuebel, Duesseldorf (DE);
Bernd Meinigke, Leverkusen (DE);
Horst Hoeffkes, Duesseldorf (DE);
Ralph Nemitz, Juechen (DE)

(73) Assignee: Henkel Kommanditgesellschaft auf Aktien (Henkel KGaA), Düsseldorf (DE)

( * ) Notice: Subject to any disclaimer, the term of this patent is extended or adjusted under 35 U.S.C. 154(b) by 0 days.

(21) Appl. No.: 11/158,939

(22) Filed: Jun. 22, 2005

(65) Prior Publication Data

US 2006/0016023 A1    Jan. 26, 2006

Related U.S. Application Data

(63) Continuation of application No. PCT/EP03/14126, filed on Dec. 12, 2003.

(30) Foreign Application Priority Data

Dec. 23, 2002  (DE) ................ 102 60 820

(51) Int. Cl.
*A61K 7/13*    (2006.01)
(52) U.S. Cl. .............. 8/405; 8/406; 8/410; 8/411; 8/415; 8/450; 8/568; 8/571; 8/574; 548/300; 544/1
(58) Field of Classification Search ........... 8/405, 8/406, 410, 411, 415, 450, 568, 571, 574; 548/300; 544/1
See application file for complete search history.

(56) References Cited

U.S. PATENT DOCUMENTS

| | | | |
|---|---|---|---|
| RE30,199 E | 1/1980 | Rose et al. | 8/10.2 |
| 4,325,704 A | 4/1982 | Konrad et al. | 8/407 |
| 4,865,774 A | 9/1989 | Fabry et al. | 252/504 |
| 4,931,218 A | 6/1990 | Schenker et al. | 252/351 |
| 4,994,087 A | 2/1991 | Konrad et al. | 8/409 |
| 5,061,289 A | 10/1991 | Clausen et al. | 8/405 |
| 5,294,726 A | 3/1994 | Bahler et al. | 554/98 |
| 5,380,340 A | 1/1995 | Neunhoeffer et al. | 8/409 |
| 5,534,267 A | 7/1996 | Neunhoeffer et al. | 424/701 |
| 5,663,366 A | 9/1997 | Neunhoeffer et al. | 548/37.4 |
| 5,766,576 A | 6/1998 | Löwe et al. | 424/62 |
| 6,099,592 A | 8/2000 | Vidal et al. | 8/409 |
| 6,204,264 B1 * | 3/2001 | Kobayashi et al. | 514/235.8 |
| 6,284,003 B1 | 9/2001 | Rose et al. | 8/412 |
| 6,383,230 B1 | 5/2002 | Genet et al. | 8/405 |

FOREIGN PATENT DOCUMENTS

| | | |
|---|---|---|
| CA | 2 445 749 | 9/2002 |
| DE | 2 359 399 A1 | 6/1975 |
| DE | 29 34 330 C2 | 3/1988 |
| DE | 37 23 354 A1 | 1/1989 |
| DE | 37 25 030 A1 | 2/1989 |
| DE | 37 41 236 A1 | 6/1989 |
| DE | 3 843 892 A1 | 6/1990 |
| DE | 39 26 344 A1 | 2/1991 |
| DE | 41 33 957 A1 | 4/1993 |
| DE | 195 43 988 A1 | 5/1997 |
| DE | 101 11 936 C1 | 10/2002 |
| EP | 0 740 931 B1 | 8/1997 |
| EP | 0 998 908 A2 | 5/2000 |
| EP | 1 022 271 A1 | 7/2000 |
| GB | 1 026 978 | 4/1966 |
| GB | 1 153 196 | 5/1969 |
| JP | 02 019576 | 1/1990 |
| WO | WO 94/08969 A1 | 4/1994 |
| WO | WO 94/08970 A1 | 4/1994 |
| WO | WO 96/15765 A1 | 5/1996 |

OTHER PUBLICATIONS

STIC Search Report dated Jan. 24, 2006.*
C. Zviak, "Nonoxidation Coloring", The Science of Hair Care, Chapter 7, pp. 248-250, published in vol. 7 of Dermatology, Marcel Dekker Inc. NY/Basle (1986).
C. Zviak, "Oxidation Colouring", The Science of Hair Care, Chapter 8, pp. 263-286, published in vol. 7 of Dermatology, Marcel Dekker Inc. NY/Basel (1986).
EU Inventory of Cosmetic Ingredients, Colipa, Mar. 1996 on diskette.
K. Schrader, Grunglagenund Rezepturen der Kosmetika, 2$^{nd}$ Editions, Huthig Buch Verlag, Heidelberg (1989).
Kornerup et al., 3$^{rd}$ Edition, Muster-Schmidt Verlag, Zurich, Gottingen (1981).

* cited by examiner

Primary Examiner—Eisa Elhilo
(74) Attorney, Agent, or Firm—John S. Child, Jr.; Stephen D. Harper

(57) ABSTRACT

Agents for coloring keratinic fibers are provided which contain specific m-phenylenediamine derivatives such as N-2-(morpholine-4-yl)ethyl-m-phenylenediamine, N-3-(morpholine-4-yl)propyl-m-phenylenediamine, and N-3-(imidazole-1-yl)-propyl-m-phenylenediamine.

16 Claims, No Drawings

M-PHENYLENEDIAMINE DERIVATIVES AS COUPLER COMPONENTS FOR THE COLORING OF KERATINIC FIBERS

CROSS REFERENCE TO RELATED APPLICATIONS

This application is a continuation under 35 U.S.C. § 365(c) and 35 U.S.C. § 120 of international application PCT/EP2003/014126, filed Dec. 12, 2003, which is incorporated herein by reference in its entirety. This application also claims priority under 35 U.S.C. § 119 of DE 102 60 820.2, filed Dec. 23, 2002, which is incorporated herein by reference in its entirety.

BACKGROUND OF THE INVENTION

The present invention concerns agents for coloring keratinic fibers, which agents contain specific m-phenylenediamine derivatives; a method for coloring hair using those agents; and certain of those m-phenylenediamine derivatives themselves and intermediate products that occur during the manufacture of those compounds.

Because of their intense colors and good fastness properties, the so-called oxidative coloring agents play a preferred role in the coloring of keratinic fibers, in particular human hair. Such coloring agents contain oxidative coloring agent precursor products, so-called developer components and coupler components. The developer components, among themselves or by coupling with one or more coupler components, form the actual dyes under the influence of oxidizing agents or atmospheric oxygen.

The developer components utilized are usually primary aromatic amines having a further free or substituted hydroxy or amino group in the para or ortho position, diaminopyridine derivatives, heterocyclic hydrazones, 4-aminopyrazolone derivatives, and 2,4,5,6-tetraaminopyrimidine and its derivatives.

Specific representatives are, for example, p-phenylenediamine, p-toluylenediamine, 2,4,5,6-tetraaminopyrimidine, p-aminophenol, N,N-bis(2-hydroxyethyl)-p-phenylenediamine, 2-(2,5-diaminophenyl) ethanol, 2-(2,5-diaminophenoxy) ethanol, 1-phenyl-3-carboxyamido-4-aminopyrazolone-5, 4-amino-3-methylphenol, 2-aminomethyl-4-aminophenol, 2-hydroxy4,5,6-triaminopyrimidine, 2,4-dihydroxy-5,6-diaminopyrimidine, 2,5,6-triamino4-hydroxypyrimidine, and 1,3-N,N'-bis(2-hydroxyethyl)-N,N'-bis(4-aminophenyl)diaminopropan-2-ol.

As a rule, m-phenylenediamine derivatives, naphthols, resorcinol and resorcinol derivatives, pyrazolones, and m-aminophenols are used as coupler components. Particularly suitable as coupler substances are 1-naphthol, 1,5-, 2,7-, and 1,7-dihydroxynaphthalene, 5-amino-2-methylphenol, m-aminophenol, resorcinol, resorcinol monomethyl ether, m-phenylenediamine, 1-phenyl-3-methypyrazolone-5, 2,4-dichloro-3-aminophenol, 1,3-bis(2,4-diaminophenoxy)propane, 2-chlororesorcinol, 4-chlororesorcinol, 2-chloro-6-methyl-3-aminophenol, 2-methylresorcinol, 5-methylresorcinol, and 2-methyl-4-chloro-5-aminophenol.

Good oxidative dye precursor products should primarily meet the following requirements: During oxidative coupling, they must form the desired color tints with sufficient intensity and fastness. They must moreover possess a good ability to absorb onto the fibers; in the case of human hair in particular, there must be no perceptible differences between grown-out and newly-grown hair (equalization capability). They should be resistant to light, heat, perspiration, abrasion, and the influence of chemical reducing agents, e.g. permanent-wave fluids. Lastly, if they are to be used as hair coloring agents, they should not impart too much color to the scalp, and most of all they need to be harmless from a toxicological and dermatological standpoint. In addition, it should be possible to easily remove from the hair, by bleaching, the coloring that is achieved, if it does not meet the particular needs of the individual person and needs to be reversed.

It is generally not possible to achieve a color tint that looks natural on the hair using only one developer component or one specific coupler/developer combination. In practice, therefore, combinations of different developer and/or coupler components are usually used. There is therefore a continual need for new, improved dye components that are also unproblematic in terms of toxicology and dermatology.

SUMMARY OF THE INVENTION

It was therefore the object of the present invention to develop new coupler components that meet the criteria applied to oxidative dye precursor products, especially in terms of toxicological and dermatological properties, and that make possible color over a wide color spectrum with good fastness properties.

It has been found, surprisingly, that the present m-phenylenediamine derivatives make possible color results with high color intensities, good light fastness and washing fastness properties, and a good equalization capability.

DETAILED DESCRIPTION OF CERTAIN EMBODIMENTS OF THE INVENTION

A first subject of the present invention is therefore agents for coloring keratinic fibers, in particular human hair, containing as coupler component, in a cosmetically acceptable carrier, at least one m-phenylenediamine derivative of formula (I)

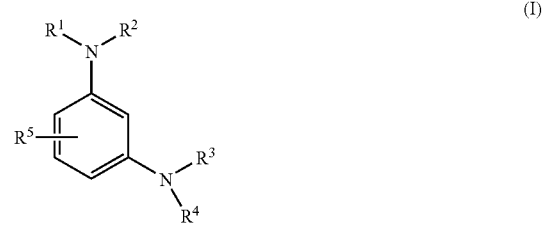

where the radicals $R^1$, $R^2$, $R^3$, and $R^4$ denote, independently of one another, a hydrogen atom, a $C_1$ to $C_4$ alkyl group, a $C_2$ to $C_6$ monohydroxyalkyl group, a $C_3$ to $C_6$ polyhydroxyalkyl group, a $C_1$ to $C_4$ alkoxy($C_1$ to $C_4$ alkyl) group, or a radical of formula (II)

 —X—Het (II)

where

X denotes a saturated alkylene group having 2 to 6 carbon atoms, for example a linear or branched alkylene chain, an alkylene ring, or mixed forms thereof, which optionally can carry one or more substituents selected from: a hydroxy group, a $C_1$ to $C_4$ alkoxy group, or a halogen atom; and Het denotes a 5-, 6-, or 7-member monocyclic, uncharged heterocycle that contains at least one nitrogen atom, one oxygen atom, or one sulfur atom, and optionally can carry up to two substituents other than hydrogen that are selected from: a $C_1$ to $C_4$ alkyl group, a $C_1$ to $C_4$ monohydroxyalkyl group, a $C_1$ to $C_4$ monoaminoalkyl group, a $C_1$ to $C_4$ alkoxy group, a hydroxy group, or an amino group optionally substituted with one or two $C_1$ to $C_4$ alkyl group(s); and $R^5$ denotes a hydrogen atom, a halogen atom, a $C_1$ to $C_4$ alkyl group, a $C_1$ to $C_4$ monohydroxyalkyl group, a $C_2$ to $C_4$ polyhydroxyalkyl group, a $C_1$ to $C_4$ alkoxy($C_1$ to $C_4$ alkyl) group, or a $C_1$ to $C_4$ alkoxy group, with the stipulation that at least one of the radicals $R^1$, $R^2$, $R^3$, or $R^4$ denotes a radical of formula (II).

"Keratinic fibers" are understood according to the present invention to be furs, wool, feathers, and in particular human hair. Although the oxidative coloring agents according to the present invention are suitable primarily for coloring keratinic fibers, there is no obstacle, in principle, to utilization in other areas as well, in particular in color photography.

Because the m-phenylenediamine derivatives according to the present invention are amino compounds, the known acid addition salts can be produced from them in the usual way. All statements in this document, and accordingly in the range of protection that is claimed, therefore refer both to the compounds present in the free state and to their water-soluble, physiologically compatible salts. Examples of such salts are the hydrochlorides, hydrobromides, sulfates, phosphates, acetates, propionates, citrates, and lactates. The hydrochlorides and sulfates are particularly preferred.

Examples of the $C_1$ to $C_4$ alkyl groups mentioned as substituents in the compounds according to the present invention are the methyl, ethyl, propyl, isopropyl, and butyl groups. Ethyl and methyl are preferred alkyl groups. Preferred $C_1$ to $C_4$ alkoxy groups are the methoxy and ethoxy groups. A hydroxymethyl, 2-hydroxyethyl, 3-hydroxypropyl, or 4-hydroxybutyl group may furthermore be mentioned as preferred examples of a $C_1$ to $C_6$ monohydroxyalkyl group. A 2-hydroxyethyl group is particularly preferred. A particularly preferred $C_2$ to $C_6$ polyhydroxyalkyl group is the 1,2-dihydroxyethyl group for the case in which the polyhydroxyalkyl group is bound directly to the aromatic system, and the 2,3-dihydroxypropyl group for the case in which the polyhydroxyalkyl group is bound to a nitrogen atom. Examples of halogen atoms are, according to the present invention, F, Cl, or Br atoms. Cl atoms are very particularly preferred.

The other designations used are derived from the definitions given here.

The m-phenylenediamine derivatives of formula (I) can be produced using conventional organic methods. The reader is referred at this point, by way of example, to the experimental protocols in the context of the exemplifying embodiments.

The m-phenylenediamine derivatives according to the present invention have not previously been described in the existing art. Some documents do, however, describe structurally related compounds. For example, DE Unexamined Application 37 41 236, DE-A1-29 34 330, and DE-C1-101 11 936 describe m-phenylenediamine derivatives that carry, on one nitrogen atom, heterocycles bridged via a methylene group. These documents provide absolutely no information, however, as to the outstanding coloring properties of the m-phenylenediamines presently claimed. In addition, the color results achieved with the present m-phenylenediamine derivatives, in combination with p-phenylenediamine and its derivatives, are distinguished by an improved color tint stability on the hair as compared with compounds of the existing art. The red shift of the color tints that is otherwise often observed is therefore much less apparent with the present m-phenylenediamine derivatives, or is in fact entirely absent.

According to the present invention, the m-phenylenediamine derivatives of formula (I) in which one of the two radicals $R^1$ and $R^2$ and one of the two radicals $R^3$ and $R^4$ denotes a group of formula (II) can be preferred. The compounds that carry asymmetrically substituted amino groups can be particularly preferred in this context.

The m-phenylenediamine derivatives of formula (I) in which only one of the radicals $R^1$, $R^2$, $R^3$, and $R^4$ denotes a group of formula (II) can also, however, be preferred according to the present invention.

It is preferred according to the present invention if the radicals $R^1$, $R^2$, $R^3$, and $R^4$ that do not denote a group of formula (I) denote, independently of one another, a hydrogen atom, a methyl group, or a 2-hydroxyethyl group. It can be preferred according to the present invention for all radicals $R^1$, $R^2$, $R^3$, and $R^4$ that do not denote a group of formula (II) to be hydrogen atoms.

According to the present invention, m-phenylenediamine derivatives of formula (I) in which X denotes an alkylene group having 2 to 4 carbon atoms can also be preferred. Particularly preferred are m-phenylenediamine derivatives of formula (I) in which X denotes an ethylene group or a propylene group. Compounds of formula (I) in which X denotes a propylene group are very particularly preferred.

Particularly preferred are m-phenylenediamine derivatives of formula (I) in which Het denotes a saturated, unsaturated, or aromatic 5- or 6-member ring system having at least one hetero atom. Heterocyclic ring systems that contain at least one nitrogen atom can be preferred according to the present invention. If the heterocyclic ring system contains a nitrogen atom, it can be preferred according to the present invention if the ring system is bound to the X radical via that nitrogen atom. Particularly preferred are m-phenylenediamine derivatives of formula (I) in which Het denotes a furanyl radical, a pyrrolyl radical, a pyrrolidinyl radical, a piperidinyl radical, a pyrazolyl radical, an oxazolyl radical, a triazolyl radical, a morpholinyl radical, an imidazolyl radical, a thiazolyl radical, an isoxazolyl radical, an isothiazolyl radical, or a piperazinyl radical.

m-Phenylenediamine derivatives of formula (I) in which Het denotes a morpholin-4-yl radical or an imidazol-1-yl radical are very particularly preferred.

Also preferred according to the present invention are compounds of formula (I) in which $R^5$ denotes a hydrogen atom or a methyl group. Those compounds in which $R^5$ denotes hydrogen can be particularly preferred.

Particularly preferred according to the present invention are m-phenylenediamine derivatives of formula (I) that are selected from the group constituted by N-2-(morpholin-4-yl)ethyl-m-phenylenediamine, N-3-(morpholin-4-yl)propyl-m-phenylenediamine, and N-3-(imidazol-1-yl)-propyl-m-phenylenediamine. N-3-(imidazol-1-yl)-propyl-m-phenylenediamine is a very particularly preferred m-phenylenediamine derivative of formula (I).

In addition to the m-phenylenediamine derivatives of formula (I), the coloring agents according to the present invention can furthermore contain at least one developer component.

Primary aromatic amines having a further free or substituted hydroxy or amino group in the para or ortho position, diaminopyridine derivatives, heterocyclic hydrazones, 4-aminopyrazole derivatives, and 2,4,5,6-tetraaminopyrimidine and its derivatives, are usually used as developer components.

It can be preferred according to the present invention to use as the developer component a p-phenylenediamine derivative or one of its physiologically compatible salts. Particularly preferred are p-phenylenediamine derivatives of formula (E1):

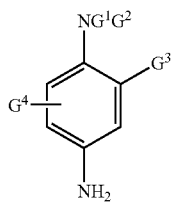

(E1)

where
- $G^1$ denotes a hydrogen atom, a $C_1$ to $C_4$ alkyl radical, a $C_1$ to $C_4$ monohydroxyalkyl radical, a $C_2$ to $C_4$ polyhydroxyalkyl radical, a ($C_1$ to $C_4$) alkoxy($C_1$ to $C_4$) alkyl radical, a 4'-aminophenyl radical, or a $C_1$ to $C_4$ alkyl radical that is substituted with a nitrogen-containing group, a phenyl radical, or a 4'-aminophenyl radical;
- $G^2$ denotes a hydrogen atom, a $C_1$ to $C_4$ alkyl radical, a $C_1$ to $C_4$ monohydroxyalkyl radical, a $C_2$ to $C_4$ polyhydroxyalkyl radical, a ($C_1$ to $C_4$) alkoxy($C_1$ to $C_4$) alkyl radical, or a $C_1$ to $C_4$ alkyl radical that is substituted with a nitrogen-containing group;
- $G^3$ denotes a hydrogen atom, a halogen atom such as a chlorine, bromine, iodine, or fluorine atom, a $C_1$ to $C_4$ alkyl radical, a $C_1$ to $C_4$ monohydroxyalkyl radical, a $C_2$ to $C_4$ polyhydroxyalkyl radical, a $C_1$ to $C_4$ hydroxyalkoxy radical, a $C_1$ to $C_4$ acetylaminoalkoxy radical, a $C_1$ to $C_4$ mesylaminoalkoxy radical, or a $C_1$ to $C_4$ carbamoylaminoalkoxy radical;
- $G^4$ denotes a hydrogen atom, a halogen atom, or a $C_1$ to $C_4$ alkyl radical or,
- if $G^3$ and $G^4$ are in the ortho position with respect to one another, they can together constitute a bridging α,ω-alkylenedioxo group such as, for example, an ethylenedioxy group.

Examples of the $C_1$ to $C_4$ alkyl radicals mentioned as substituents in the compounds according to the present invention are the methyl, ethyl, propyl, isopropyl, and butyl groups. Ethyl and methyl are preferred alkyl radicals. $C_1$ to $C_4$ alkoxy radicals that are preferred according to the present invention are, for example, a methoxy or an ethoxy group. A hydroxymethyl, 2-hydroxyethyl, 3-hydroxypropyl, or 4-hydroxybutyl group can furthermore be mentioned as preferred examples for a $C_1$ to $C_4$ hydroxyalkyl group. A 2-hydroxyethyl group is particularly preferred. A particularly preferred $C_2$ to $C_4$ polyhydroxyalkyl group is the 1,2-dihydroxyethyl group. Examples of halogen atoms according to the present invention are F, Cl, or Br atoms; Cl atoms are very particularly preferred. The additional terms that are used are derived, according to the present invention, from the definitions given here. Examples of nitrogen-containing groups of formula (E1) are, in particular, the amino groups, $C_1$ to $C_4$ monoalkylamino groups, $C_1$ to $C_4$ dialkylamino groups, $C_1$ to $C_4$ trialkylammonium groups, $C_1$ to $C_4$ monohydroxyalkylamino groups, imidazolinium, and ammonium.

Particularly preferred p-phenylenediamines of formula (E1) are selected from p-phenylenediamine, p-toluylenediamine, 2-chloro-p-phenylenediamine, 2,3-dimethyl-p-phenylenediamine, 2,6-dimethyl-p-phenylenediamine, 2,6-diethyl-p-phenylenediamine, 2,5-dimethyl-p-phenylenediamine, N,N-dimethyl-p-phenylenediamine, N,N-diethyl-p-phenylenediamine, N,N-dipropyl-p-phenylenediamine, 4-amino-3-methyl-(N,N-diethyl)aniline, N,N-bis-(β-hydroxyethyl)-p-phenylenediamine, 4-N,N-bis-(β-hydroxyethyl)-amino-2-methylaniline, 4-N,N-bis-(β-hydroxyethyl)-amino-2-chloroaniline, 2-(β-hydroxyethyl)-p-phenylenediamine, 2-(α,β-dihydroxyethyl)-p-phenylenediamine, 2-fluoro-p-phenylenediamine, 2-isopropyl-p-phenylenediamine, N-(β-hydroxypropyl)-p-phenylenediamine, 2-hydroxymethyl-p-phenylenediamine, N,N-dimethyl-3-methyl-p-phenylenediamine, N,N-(ethyl-β-hydroxyethyl)-p-phenylenediamine, N-(β,γ-dihydroxypropyl)-p-phenylenediamine, N-(4'-aminophenyl)-p-phenylenediamine, N-phenyl-p-phenylenediamine, 2-(β-hydroxyethyloxy)-p-phenylenediamine, 2-(β-acetylaminoethyloxy)-p-phenylenediamine, N-(β-methoxyethyl)-p-phenylenediamine, and 5,8-diaminobenzo-1,4-dioxane, as well as their physiologically compatible salts.

p-Phenylenediamine derivatives of formula (E1) that are very particularly preferred according to the present invention are p-phenylenediamine, p-toluylenediamine, 2-(β-hydroxyethyl)-p-phenylenediamine, 2-(α,β-dihydroxyethyl)-p-phenylenediamine, and N,N-bis-(β-hydroxyethyl)-p-phenylenediamine.

It can furthermore be preferred according to the present invention to use as the developer component compounds that contain at least two aromatic nuclei that are substituted with amino and/or hydroxy groups.

Among the binuclear developer components that can be used in the coloring compositions according to the invention, particular mention may be made of the compounds that correspond to formula (E2) below, as well as their physiologically compatible salts:

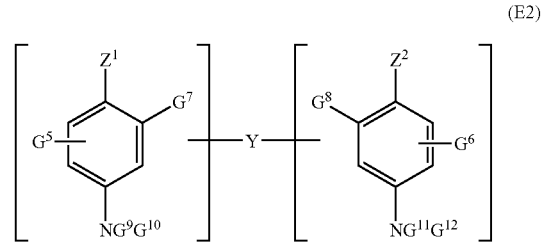

(E2)

where
- $Z^1$ and $Z^2$ denote, independently of one another, a hydroxyl or $NH_2$ radical, which if applicable is substituted with a $C_1$ to $C_4$ alkyl radical, with a $C_1$ to $C_4$ hydroxyalkyl radical, and/or with a bridge Y, or which, if applicable, is part of a bridging ring system;
- the bridge Y denotes an alkylene group having 1 to 14 carbon atoms, for example a linear or branched alkylene chain or an alkylene ring that can be interrupted or terminated by one or more nitrogen-containing groups and/or one or more hetero atoms such as oxygen, sulfur, or nitrogen atoms, and possibly can be substituted with one or more hydroxyl or $C_1$ to $C_8$ alkoxy radicals, or a direct bond;

$G^5$ and $G^6$ denote, independently of one another, a hydrogen or halogen atom, a $C_1$ to $C_4$ alkyl radical, a $C_1$ to $C_4$ monohydroxyalkyl radical, a $C_2$ to $C_4$ polyhydroxyalkyl radical, a $C_1$ to $C_4$ aminoalkyl radical, or a direct connection to bridge Y;

$G^7$, $G^8$, $G^9$, $G^{10}$, $G^{11}$, and $G^{12}$ denote, independently of one another, a hydrogen atom, a direct bond to bridge Y, or a $C_1$ to $C_4$ alkyl radical, with the stipulations that the compounds of formula (E2) contain only one bridge Y per molecule; and the compounds of formula (E2) contain at least one amino group that carries at least one hydrogen atom.

The substituents used in formula (E2) are defined, according to the present invention, by analogy with what is presented above.

Preferred binuclear developer components of formula (E2) are, in particular: N,N'-bis-(β-hydroxyethyl)-N,N'-bis-(4'-aminophenyl)-1,3-diaminopropan-2-ol, N,N'-bis-(β-hydroxyethyl)-N,N'-bis-(4'-aminophenyl)ethylenediamine, N,N'-bis-(4-aminophenyl)tetramethylenediamine, N,N'-bis-(β-hydroxyethyl)-N,N'-bis-(4-aminophenyl)tetramethylenediamine, N,N'-bis-(4-methylaminophenyl)tetramethylenediamine, N,N'-diethyl-N,N'-bis-(4'-amino-3'-methylphenyl)ethylenediamine, bis-(2-hydroxy-5-aminophenyl)methane, 1,3-bis-(2,5-diaminophenoxy)propan-2-ol, N,N'-bis-(4'-aminophenyl)-1,4-diazacycloheptane, N,N'-bis-(2-hydroxy-5-aminobenzyl)piperazine, N-(4'-aminophenyl)-p-phenylenediamine, and 1,10-bis-(2',5'-diaminophenyl)-1,4,7,10-tetraoxadecane, and their physiologically compatible salts.

Particularly preferred binuclear developer components of formula (E2) are N,N'-bis-(β-hydroxyethyl)-N,N'-bis-(4'-aminophenyl)-1,3-diaminopropan-2-ol, bis-(2-hydroxy-5-aminophenyl)methane, 1,3-bis-(2,5-diaminophenoxy)propan-2-ol, N,N'-bis-(4'-aminophenyl)-1,4-diazacycloheptane, and 1,10-bis-(2',5'-diaminophenyl)-1,4,7,10-tetraoxadecane, or one of their physiologically compatible salts.

Bis-(2-hydroxy-5-aminophenyl)methane is a very particularly preferred binuclear developer component of formula (E2). It can further be preferred according to the present invention to use as the developer component a p-aminophenol derivative or one of its physiologically compatible salts. Particularly preferred are p-aminophenol derivatives of formula (E3):

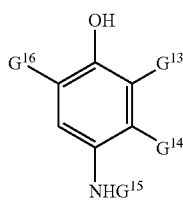

(E3)

where $G^{13}$ denotes a hydrogen atom, a halogen atom, a $C_1$ to $C_4$ alkyl radical, a $C_1$ to $C_4$ monohydroxyalkyl radical, a $C_2$ to $C_4$ polyhydroxyalkyl radical, a ($C_1$ to $C_4$) alkoxy ($C_1$ to $C_4$) alkyl radical, a $C_1$ to $C_4$ aminoalkyl radical, a hydroxy($C_1$ to $C_4$) alkylamino radical, a $C_1$ to $C_4$ hydroxyalkoxy radical, a $C_1$ to $C_4$ hydroxyalkyl($C_1$ to $C_4$) aminoalkyl radical, or a (di-$C_1$ to $C_4$-alkylamino) ($C_1$ to $C_4$) alkyl radical, and $G^{14}$ denotes a hydrogen or halogen atom, a $C_1$ to $C_4$ alkyl radical, a $C_1$ to $C_4$ monohydroxyalkyl radical, a $C_2$ to $C_4$ polyhydroxyalkyl radical, a ($C_1$ to $C_4$) alkoxy($C_1$ to $C_4$) alkyl radical, a $C_1$ to $C_4$ aminoalkyl radical, or a $C_1$ to $C_4$ cyanoalkyl radical;

$G^{15}$ denotes hydrogen, a $C_1$ to $C_4$ alkyl radical, a $C_1$ to $C_4$ monohydroxyalkyl radical, a $C_2$ to $C_4$ polyhydroxyalkyl radical, a phenyl radical, or a benzyl radical, and $G^{16}$ denotes hydrogen or a halogen atom.

The substituents used in formula (E3) are defined, according to the present invention, by analogy with what is presented above.

Preferred p-aminophenols of formula (E3) are, in particular, p-aminophenol, N-methyl-p-aminophenol, 4-amino-3-methylphenol, 4-amino-3-fluorophenol, 2-hydroxymethylamino-4-aminophenol, 4-amino-3-hydroxymethylphenol, 4-amino-2-(,-hydroxyethoxy)phenol, 4-amino-2-methylphenol, 4-amino-2-hydroxymethylphenol, 4-amino-2-methoxymethylphenol, 4-amino-2-aminomethylphenol, 4-amino-2-(β-hydroxyethylaminomethyl)phenol, 4-amino-2-(α,β-dihydroxyethyl)phenol, 4-amino-2-fluorophenol, 4-amino-2-chlorophenol, 4-amino-2,6-dichlorophenol, 4-amino-2-(diethylaminomethyl)phenol, and their physiologically compatible salts.

Very particularly preferred compounds of formula (E3) are p-aminophenol, 4-amino-3-methylphenol, 4-amino-2-aminomethylphenol, 4-amino-2-(α,β-dihydroxyethyl)phenol, and 4-amino-2-(diethylaminomethyl)phenol.

The developer component can furthermore be selected from o-aminophenol and its derivatives, for example, 2-amino-4-methylphenol, 2-amino-5-methylphenol, or 2-amino-2-chlorophenol.

The developer component can, in addition, be selected from heterocyclic developer components such as, for example, the pyridine, pyrimidine, pyrazole, pyrazole-pyrimidine derivatives and their physiologically compatible salts.

Preferred pyridine derivatives are, in particular, the compounds that are described in Great Britain patents GB 1026 978 and GB 1 153 196, such as 2,5-diaminopyridine, 2-(4'-methoxyphenyl)amino-3-aminopyridine, 2,3-diamino-6-methoxypyridine, 2-(β-methoxyethyl)amino-3-amino-6-methoxypyridine, and 3,4-diaminopyridine.

Preferred pyrimidine derivatives are, in particular, the compounds described in German patent DE 2 359 399, Japanese Unexamined Application JP 02019576 A2, or Unexamined Application WO 96/15765, such as 2,4,5,6-tetraaminopyrimidine, 4-hydroxy-2,5,6-triaminopyrimidine, 2-hydroxy-4,5,6-triaminopyrimidine, 2-dimethylamino-4,5,6-triaminopyrimidine, 2,4-dihydroxy-5,6-diaminopyrimidine, and 2,5,6-triaminopyrimidine.

Preferred pyrazole derivatives are, in particular, the compounds described in patents DE 3 843 892, DE 4 133 957, and patent applications WO 94/08969, WO 94/08970, EP-740 931, and DE 195 43 988, for example 4,5-diamino-1-methylpyrazole, 4,5-diamino-1-(β-hydroxyethyl)pyrazole, 3,4-diaminopyrazole, 4,5-diamino-1-(4'-chlorobenzyl)pyrazole, 4,5-diamino-1,3-dimethylpyrazole, 4,5-diamino-3-methyl-1-phenylpyrazole, 4,5-diamino-1-methyl-3-phenylpyrazole, 4-amino-1,3-dimethyl-5-hydrazinopyrazole, 1-benzyl-4,5-diamino-3-methylpyrazole, 4,5-diamino-3-tert-butyl-1-methylpyrazole, 4,5-diamino-1-tert-butyl-3-methylpyrazole, 4,5-diamino-1-(β-hydroxyethyl)-3-methypyrazole, 4,5-diamino-1-ethyl-3-methylpyrazole, 4,5-diamino-1-ethyl-3-(4'-methoxyphenyl)pyrazole, 4,5-diamino-1-ethyl-3-hydroxymethylpyrazole, 4,5-diamino-3-hydroxymethyl-1-methylpyrazole, 4,5-diamino-3-hydroxymethyl-1-isopropylpyrazole, 4,5-diamino-3- methyl-1-isopropylpyrazole, 4-amino-5-(β-aminoethyl)amino-1,3-dimethylpyrazole, 3,4,5-triaminopyrazole, 1-methyl-3,4,5-triaminopyrazole, 3,5-diamino-1-methyl-4-methylaminopyrazole, and 3,5-diamino-4-(β-hydroxyethyl)amino-1-methylpyrazole.

Preferred pyrazole-pyrimidine derivatives are, in particular, derivatives of pyrazole-[1,5-a]-pyrimidine of the following formula (E4) and their tautomeric forms, provided a tautomeric equilibrium exists:

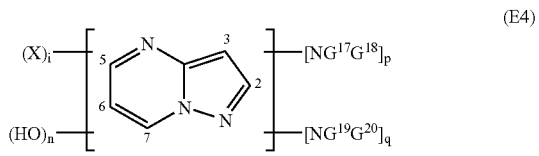
(E4)

where
G$^{17}$, G$^{18}$, G$^{19}$, and G$^{20}$ denote, independently of one another, a hydrogen atom, a $C_1$ to $C_4$ alkyl radical, an aryl radical, a $C_1$ to $C_4$ hydroxyalkyl radical, a $C_2$ to $C_4$ polyhydroxyalkyl radical, a ($C_1$ to $C_4$) alkoxy($C_1$ to $C_4$) alkyl radical, a $C_1$ to $C_4$ aminoalkyl radical that can, if applicable, be protected by an acetyl ureide or sulfonyl radical, a ($C_1$ to $C_4$) alkylamino($C_1$ to $C_4$) alkyl radical, a di-[($C_1$ to $C_4$) alkyl]($C_1$ to $C_4$) aminoalkyl radical, the dialkyl radicals constituting, if applicable, a carbon cycle or a heterocycle having 5 or 6 chain members, a $C_1$ to $C_4$ hydroxyalkyl or di-($C_1$ to $C_4$) [hydroxyalkyl] ($C_1$ to $C_4$) aminoalkyl radical.

the X radicals denote, independently of one another, a hydrogen atom, a $C_1$ to $C_4$ alkyl radical, an aryl radical, a $C_1$ to $C_4$ hydroxyalkyl radical, a $C_2$ to $C_4$ polyhydroxyalkyl radical, a $C_1$ to $C_4$ aminoalkyl radical, a ($C_1$ to $C_4$) alkylamino($C_1$ to $C_4$) alkyl radical, a di-[($C_1$ to $C_4$) alkyl]($C_1$ to $C_4$) aminoalkyl radical, the dialkyl radicals constituting, if applicable, a carbon cycle or a heterocycle having 5 or 6 chain members, a $C_1$ to $C_4$ hydroxyalkyl radical or di-($C_1$ to $C_4$ hydroxyalkyl) aminoalkyl radical, an amino radical, a $C_1$ to $C_4$ alkyl or di-($C_1$ to $C_4$ hydroxyalkyl)amino radical, a halogen atom, a carboxylic acid group, or a sulfonic acid group.

i has the value 0, 1, 2, or 3;
p has the value 0 or 1;
q has the value 0 or 1; and
n has the value 0 or 1, with the stipulation that
the sum of p+q is not equal to 0;
if p+q=2, n has the value 0, and the NG$^{17}$G$^{18}$ and NG$^{19}$G$^{20}$ groups occupy positions (2,3), (5,6), (6,7), (3,5), or (3,7);
if p+q=1, n has the value 1, and the NG$^{17}$G$^{18}$ (or NG$^{19}$G$^{20}$) groups and the OH group occupy the positions (2,3), (5,6), (6,7), (3,5), or (3,7).

The substituents used in formula (E4) are defined, according to the present invention, by analogy with what is presented above.

If the pyrazole-[1,5-a]-pyrimidine of the above formula (E4) contains a hydroxy group at one of positions 2, 5, or 7 of the ring system, a tautomeric equilibrium exists that can be depicted, for example, in the following diagram:

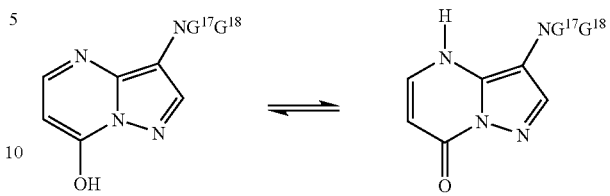

Among the pyrazole-[1,5-a]-pyrimidines of the above formula (E4) that may be mentioned are, in particular:
pyrazole-[1,5-a]-pyrimidine-3,7-diamine;
2,5-dimethylpyrazole-[1,5-a]-pyrimidine-3,7-diamine;
pyrazole-[1,5-a]-pyrimidine-3,5-diamine;
2,7-dimethylpyrazole-[1,5-a]-pyrimidine-3,5-diamine;
3-aminopyrazole-[1,5-a]-pyrimidin-7-ol;
3-aminopyrazole-[1,5-a]-pyrimidin-5-ol;
2-(3-aminopyrazole-[1,5-a]-pyrimidin-7-ylamino) ethanol;
2-(7-aminopyrazole-[1,5-a]-pyrimidin-3-ylamino) ethanol;
2-[(3-aminopyrazole-[1,5-a]-pyrimidin-7-yl)-(2-hydroxyethyl)amino]ethanol;
2-[(7-aminopyrazole-[1,5-a]-pyrimidin-3-yl)-(2-hydroxyethyl)amino]ethanol;
5,6-dimethylpyrazole-[1,5-a]-pyrimidine-3,7-diamine;
2,6-dimethylpyrazole-[1,5-a]-pyrimidine-3,7-diamine;
3-amino-7-dimethylamino-2,5-dimethylpyrazole-[1,5-a]-pyrimidine, and their physiologically compatible salts and tautomeric forms, if a tautomeric equilibrium exists.

The pyrazole-[1,5-a]-pyrimidines of the above formula (E4) can be produced, as described in the literature, by cyclization proceeding from an aminopyrazole or from hydrazine.

In a further preferred embodiment, the coloring agents according to the present invention contain at least one further coupler component.

As a rule, m-phenylenediamine derivatives, naphthols, resorcinol and resorcinol derivatives, pyrazolones, and m-aminophenol derivatives are used as coupler components. Particularly suitable as coupler substances are 1-naphthol, 1,5-, 2,7- and 1,7-dihydroxynaphthalene, 5-amino-2-methylphenol, m-aminophenol, resorcinol, resorcinol monomethyl ether, m-phenylenediamine, 1-phenyl-3-methylpyrazolone-5, 2,4-dichloro-3-aminophenol, 1,3-bis(2',4'-diaminophenoxy)propane, 2-chlororesorcinol, 4-chlororesorcinol, 2-chloro-6-methyl-3-aminophenol, 2-amino-3-hydroxypyridine, 2-methylresorcinol, 5-methylresorcinol, and 2-methyl-4-chloro-5-aminophenol.

Coupler components preferred according to the present invention are:
m-aminophenol and its derivatives, for example 5-amino-2-methylphenol, N-cyclopentyl-3-aminophenol, 3-amino-2-chloro-6-methylphenol, 2-hydroxy-4-aminophenoxy ethanol, 2,6-dimethyl-3-aminophenol, 3-trifluoroacetylamino-2-chloro-6-methylphenol, 5-amino-4-chloro-2-methylphenol, 5-amino-4-methoxy-2-methylphenol, 5-(2'-hydroxyethyl)amino-2-methylphenol, 3-(diethylamino)phenol, N-cyclopentyl-3- aminophenol, 1,3-dihydroxy-5-(methylamino)benzene, 3-ethylamino-4-methylphenol, and 2,4-dichloro-3-aminophenol;

o-aminophenol and its derivatives;

m-diaminobenzene and its derivatives, for example, 2,4-diaminophenoxy ethanol, 1,3-bis-(2',4'-diaminophenoxy)propane, 1-methoxy-2-amino-4-(2'-hydroxyethylamino)benzene, 1,3-bis-(2',4'-diaminophenyl)propane, 2,6-bis-(2'-hydroxyethylamino)-1-methylbenzene, and 1-amino-3-bis-(2'-hydroxyethyl)aminobenzene.;

o-diaminobenzene and its derivatives, for example, 3,4-diaminobenzoic acid and 2,3-diamino-1-methylbenzene;

di- or trihydroxybenzene derivatives such as, for example, resorcinol, resorcinol monomethyl ether, 2-methylresorcinol, 5-methylresorcinol, 2,5-dimethylresorcinol, 2-chlororesorcinol, 4-chlororesorcinol, pyrogallol, and 1,2,4-trihydroxybenzene;

pyridine derivatives such as, for example, 2,6-dihydroxypyridine, 2-amino-3-hydroxypyridine, 2-amino-5-chloro-3-hydroxypyridine, 3-amino-2-methylamino-6-methoxypyridine, 2,6-dihydroxy-3,4-dimethylpyridine, 2,6-dihydroxy-4-methylpyridine, 2,6-diaminopyridine, 2,3-diamino-6-methoxypyridine, and 3,5-diamino-2,6-dimethoxypyridine;

naphthalene derivatives such as, for example, 1-naphthol, 2-methyl-1-naphthol, 2-hydroxymethyl-1-naphthol, 2-hydroxyethyl-1-naphthol, 1,5-dihydroxynaphthalene, 1,6-dihydroxynaphthalene, 1,7-dihydroxynaphthalene, 1,8-dihydroxynaphthalene, 2,7-dihydroxynaphthalene, and 2,3-dihydroxynaphthalene;

morpholine derivatives such as, for example, 6-hydroxybenzomorpholine and 6-aminobenzomorpholine;

quinoxaline derivatives such as, for example, 6-methyl-1,2,3,4-tetrahydroquinoxaline;

pyrazole derivatives such as, for example, 1-phenyl-3-methylpyrazol-5-one;

indole derivatives such as, for example, 4-hydroxyindole, 6-hydroxyindole, and 7-hydroxyindole;

pyrimidine derivatives such as, for example, 4,6-diaminopyrimidine, 4-amino-2,6-dihydroxypyrimidine, 2,4-diamino-6-hydroxypyrimidine, 2,4,6-trihydroxypyrimidine, 2-amino-4-methylpyrimidine, 2-amino-4-hydroxy-6-methylpyrimidine, and 4,6-dihydroxy-2-methylpyrimidine; or methylenedioxybenzene derivatives such as, for example, 1-hydroxy-3,4-methylenedioxybenzene, 1-amino-3,4-methylenedioxybenzene, and 1-(2'-hydroxyethyl)amino-3,4-methylenedioxybenzene.

Coupler components particularly preferred according to the present invention are 1-naphthol, 1,5-, 2,7-, and 1,7-dihydroxynaphthalene, 3-aminophenol, 5-amino-2-methylphenol, 2-amino-3-hydroxypyridine, resorcinol, 4-chlororesorcinol, 2-chloro-6-methyl-3-aminophenol, 2-methylresorcinol, 5-methylresorcinol, 2,5-dimethylresorcinol, and 2,6-dihydroxy-3,4-dimethylpyridine.

The following coupler/developer combinations have proven particularly suitable according to the present invention:

N-3-(imidazol-1-yl)propyl-m-phenylenediamine/p-toluylenediamine;

N-3-(imidazol-1-yl)propyl-m-phenylenediamine/1-(2-hydroxyethyl)-4,5-diaminopyrazole.

Both combinations make possible intense blue/violet color results with very good to good fastness properties.

The hair coloring agents according to the present invention preferably contain both the developer components and the coupler components in a quantity of 0.005 to 20 wt %, preferably 0.1 to 5 wt %, in each case relative to the entire oxidative coloring agent. The developer components and coupler components are generally used in approximately molar quantities with respect to one another. Although molar utilization has proven useful, a certain excess of individual oxidative dye precursor products is not disadvantageous, so that the developer components and coupler components can be present in a molar ratio from 1:0.5 to 1:3, in particular 1:1 to 1:2.

In a further embodiment of the present invention, the coloring agents can contain at least one precursor of a nature-analogous dye. The precursors of nature-analogous dyes that are preferably used are those indoles and indolines that comprise at least one hydroxy or amino group, preferably as substituent on the six-membered ring. These groups can carry further substituents, e.g., in the form of an etherification or esterification of the hydroxy group, or an alkylation of the amino group. In a second preferred embodiment, the coloring agents contain at least one indole derivative and/or indoline derivative.

Particularly suitable as precursors of nature-analogous hair dyes are derivatives of 5,6-dihydroxyindoline, of formula (IIa):

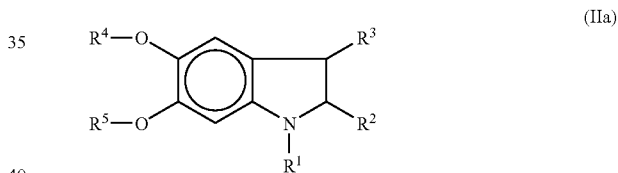

in which, independently of one another:

$R^1$ denotes hydrogen, a $C_1$–$C_4$ alkyl group, or a $C_1$–$C_4$ hydroxyalkyl group;

$R^2$ denotes hydrogen or a —COOH group, such that the —COOH group can also be present as a salt with a physiologically compatible cation;

$R^3$ denotes hydrogen or a $C_1$–$C_4$ alkyl group;

$R^4$ denotes hydrogen, a $C_1$–$C_4$ alkyl group, or a —CO—$R^6$ group in which $R^6$ denotes a $C_1$–$C_4$ alkyl group; and $R^5$ denotes one of the groups cited under $R^4$, as well as physiologically compatible salts of these compounds with an organic or inorganic acid.

Particularly preferred derivatives of indoline are 5,6-dihydroxyindoline, N-methyl-5,6-dihydroxyindoline, N-ethyl-5,6-dihydroxyindoline, N-propyl-5,6-dihydroxyindoline, N-butyl-5,6-dihydroxyindoline, 5,6-dihydroxyindoline-2-carboxylic acid, as well as 6-hydroxyindoline, 6-aminoindoline, and 4-aminoindoline.

Particularly to be emphasized within this group are N-methyl-5,6-dihydroxyindoline, N-ethyl-5,6-dihydroxyindoline, N-propyl-5,6-dihydroxyindoline, N-butyl-5,6-dihydroxyindoline, and in particular 5,6-dihydroxyindoline.

Outstandingly suitable, in addition, as precursors of nature-analogous hair dyes are derivatives of 5,6-dihydroxyindoline of formula (IIb):

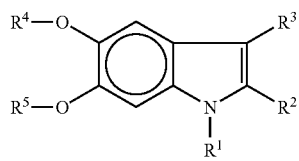

(IIb)

in which, independently of one another, $R^1$ denotes hydrogen, a $C_1$–$C_4$ alkyl group, or a $C_1$–$C_4$ hydroxyalkyl group;

$R^2$ denotes hydrogen or a —COOH group, such that the —COOH group can also be present as a salt with a physiologically compatible cation;

$R^3$ denotes hydrogen or a $C_1$–$C_4$ alkyl group;

$R^4$ denotes hydrogen, a $C_1$–$C_4$ alkyl group, or a —CO—$R^6$ group in which $R^6$ denotes a $C_1$–$C_4$ alkyl group; and $R^5$ denotes one of the groups cited under $R^4$, as well as physiologically compatible salts of these compounds with an organic or inorganic acid.

Particularly preferred derivatives of indole are 5,6-dihydroxyindole, N-methyl-5,6-dihydroxyindole, N-ethyl-5,6-dihydroxyindole, N-propyl-5,6-dihydroxyindole, N-butyl-5,6-dihydroxyindole, 5,6-dihydroxyindole-2-carboxylic acid, 6-hydroxyindole, 6-aminoindole, and 4-aminoindole.

To be emphasized within this group are N-methyl-5,6-dihydroxyindole, N-ethyl-5,6-dihydroxyindole, N-propyl-5,6-dihydroxyindole, N-butyl-5,6-dihydroxyindole, and in particular 5,6-dihydroxyindole.

The indoline and indole derivatives can be used in the coloring agents according to the present invention both as free bases and in the form of their physiologically compatible salts with inorganic or organic acids, e.g. the hydrochlorides, sulfates, and hydrobromides. The indole or indoline derivatives are usually contained therein in quantities of 0.05 to 10 wt %, preferably 0.2 to 5 wt %.

In a further embodiment, provision can be made according to the present invention to use the indoline or indole derivative in coloring agents in combination with at least one amino acid or oligopeptide. The amino acid is advantageously an alpha-amino acid; very particularly preferred alpha-amino acids are arginine, ornithine, lysine, serine, and histidine, in particular arginine.

In addition to the m-phenylenediamine derivatives of formula (I) according to the present invention, in a further preferred embodiment of the present invention the coloring agents according to the present invention can contain one or more direct-absorbing dyes for color tinting. Direct-absorbing dyes are usually nitrophenylenediamines, nitroaminophenols, azo dyes, anthraquinones, or indophenols. Preferred direct-absorbing dyes are the compounds known under the international designations or trade names HC Yellow 2, HC Yellow 4, HC Yellow 5, HC Yellow 6, HC Yellow 12, Acid Yellow 1, Acid Yellow 10, Acid Yellow 23, Acid Yellow 36, HC Orange 1, Disperse Orange 3, Acid Orange 7, HC Red 1, HC Red 3, HC Red 10, HC Red 11, HC Red 13, Acid Red 33, Acid Red 52, HC Red BN, Pigment Red 57:1, HC Blue 2, HC Blue 12, Disperse Blue 3, Acid Blue 7, Acid Green 50, HC Violet 1, Disperse Violet 1, Disperse Violet 4, Acid Violet 43, Disperse Black 9, Acid Black 1, and Acid Black 52, as well as 1,4-diamino-2-nitrobenzene, 2-amino4-nitrophenol, 1,4-bis-(β-hydroxyethyl)amino-2-nitrobenzene, 3-nitro-4-(β-hydroxyethyl)aminophenol, 2-(2'-hydroxyethyl)amino-4,6-dinitrophenol, 1-(2'-hydroxyethyl)amino-4-methyl-2-nitrobenzene, 1-amino4-(2'-hydroxyethyl)amino-5-chloro-2-nitrobenzene, 4-amino-3-nitrophenol, 1-(2'-ureidoethyl)amino-4-nitrobenzene, 4-amino-2-nitrodiphenylamine-2'-carboxylic acid, 6-nitro-1,2,3,4-tetrahydroquinoxaline, 2-hydroxy-1,4-naphthoquinone, picramic acid and its salts, 2-amino-6-chloro-4-nitrophenol, 4-ethylamino-3-nitrobenzoic acid, and 2-chloro-6-ethylamino-1-hydroxy4-nitrobenzene.

The agents according to the present invention can furthermore contain a cationic direct-absorbing dye. Particularly preferred in this context are:

(a) cationic triphenylmethane dyes such as, for example, Basic Blue 7, Basic Blue 26, Basic Violet 2, and Basic Violet 14;

(b) aromatic systems that are substituted with a quaternary nitrogen group, such as, for example, Basic Yellow 57, Basic Red 76, Basic Blue 99, Basic Brown 16, and Basic Brown 17; and (c) direct-absorbing dyes that contain a heterocycle which comprises at least one quaternary nitrogen atom, as recited, for example, in EP-A2-998 908, to which reference is explicitly made at this juncture, in claims 6 to 11.

Preferred cationic direct-absorbing dyes of group (c) are, in particular, the following compounds:

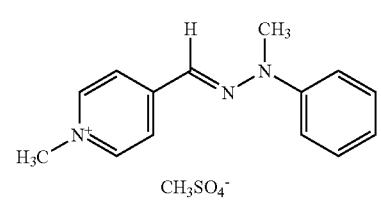

(DZ1)

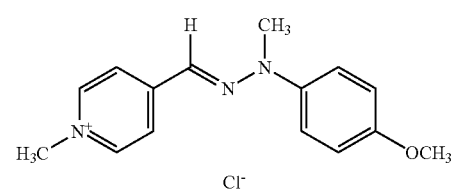

(DZ2)

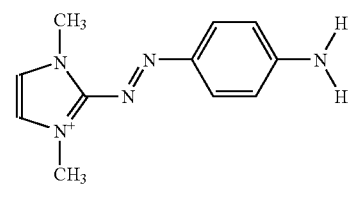

(DZ3)

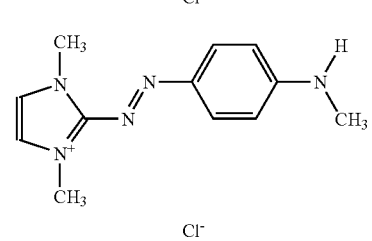

(DZ4)

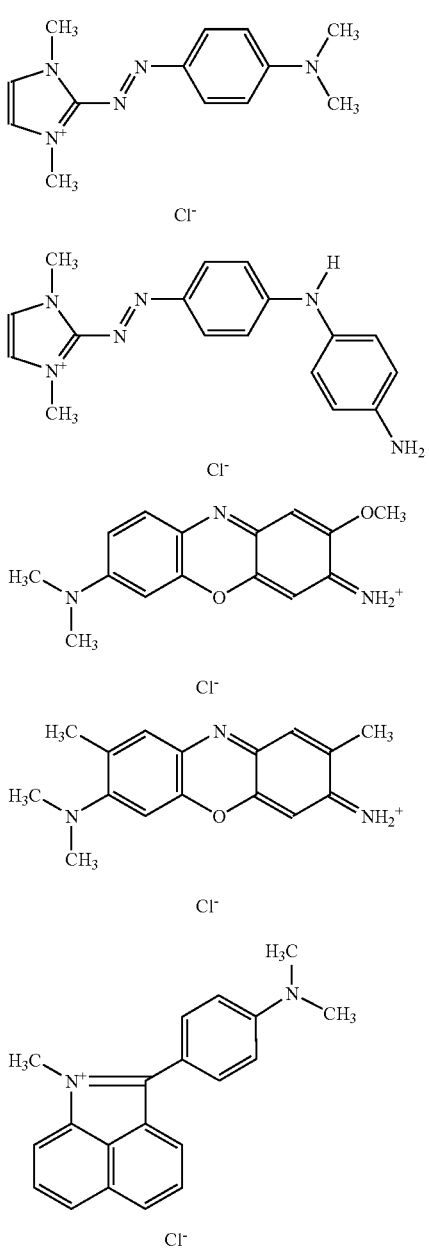

The compounds of formulas (DZ1), (DZ3), and (DZ5), which are also known under the designations Basic Yellow 87, Basic Orange 31, and Basic Red 51, are very particularly preferred cationic direct-absorbing dyes of group (c).

The cationic direct-absorbing dyes that are marketed under the trademark Arianor® are, according to the present invention, likewise very particularly preferred cationic direct-absorbing dyes.

The agents according to the present invention in accordance with this embodiment preferably contain the direct-absorbing dyes in a quantity of 0.01 to 20 wt %, relative to the entire coloring agent.

In addition, the preparations according to the present invention can also contain dyes occurring in nature, for example such as those contained in henna red, henna neutral, henna black, chamomile blossom, sandalwood, black tea, buckthorn bark, salvia, logwood, madder root, catechu, Spanish cedar, and alkanna root.

It is not necessary for the oxidative dye precursor products or the direct-absorbing dyes to represent homogeneous compounds in each case. The hair coloring agents according to the present invention can instead, depending on the production methods for the individual dyes, also contain further components in subordinate quantities, provided they do not disadvantageously influence the color result or do not have to be excluded for other (e.g., toxicological) reasons.

With reference to the dyes usable in the hair coloring and toning agents according to the present invention, reference is furthermore explicitly made to the monograph of Ch. Zviak, The Science of Hair Care, Chapter 7 pp. 248–250 (direct-absorbing dyes) and Chapter 8, pages 264–267 (oxidative dye precursor products), published as Volume 7 in the "Dermatology" series (Ch. Culnan and H. Maibach, eds.), Verlag Marcel Dekker Inc., New York, Basel, 1986; and to the "European Inventory of Cosmetic Raw Materials" published by the European Community, available in diskette form from the Bundesverband Deutscher Industrie-und Handelsunternehmen für Arzneimittel, Reformwaren und Körperpflegemittel e.V. [Federation of German Industries and Manufacturing Firms for pharmaceuticals, health care goods, dietary supplements and personal hygiene products], Mannheim.

The coloring agents according to the present invention can furthermore contain all active substances, additives, and adjuvants known for such preparations. In many cases the coloring agents contain at least one surfactant, both anionic as well as zwitterionic, ampholytic, nonionic, and cationic surfactants being suitable in principle. In many cases, however, it has proven advantageous to select the surfactants from anionic, zwitterionic, or nonionic surfactants.

Suitable as anionic surfactants in preparations according to the present invention are all anionic surface-active substances suitable for use on the human body. These are characterized by a water-solubilizing anionic group such as, for example, a carboxylate, sulfate, sulfonate, or phosphate group, and a lipophilic alky group having approximately 10 to 22 carbon atoms. Glycol or polyglycol ether groups, ester, ether, and amide groups, as well as hydroxyl groups can additionally be contained in the molecule. Examples of suitable anionic surfactants are, in each case in the form of the sodium, potassium, and ammonium salts, as well as mono-, di-, and trialkanolammonium salts having two or three carbon atoms in the alkanol group:
  linear fatty acids having 10 to 22 carbon atoms (soaps);
  ethercarboxylic acids of the formula $R-O-(CH_2-CH_2-O)_x-CH_2-COOH$, in which R is a linear alkyl group having 10 to 22 carbon atoms and x=0 or 1 to 16;
  acyl sarcosides having 10 to 18 carbon atoms in the acyl group;
  acyl taurides having 10 to 18 carbon atoms in the acyl group;
  acyl isethionates having 10 to 18 carbon atoms in the acyl group;
  sulfosuccinic acid mono- and dialkyl esters having 8 to 18 carbon atoms in the alkyl group, and sulfosuccinic acid monoalkylpolyoxyethyl esters having 8 to 18 carbon atoms in the alkyl group and 1 to 6 oxyethyl groups;
  linear alkanesulfonates having 12 to 18 carbon atoms;
  linear alpha-olefinsulfonates having 12 to 18 carbon atoms;
  alpha-sulfo fatty acid methyl esters of fatty acids having 12 to 18 carbon atoms;

alkyl sulfates and alkyl polyglycol ether sulfates of the formula R—O—(CH$_2$—CH$_2$—O)X—SO$_3$H, in which R is a preferably linear alkyl group having 10 to 18 carbon atoms and x=0 or 1 to 12;

mixtures of surface-active hydroxysulfonates, according to DE-A-37 25 030;

sulfated hydroxyalkylpolyethylene and/or hydroxyalkylenepropylene glycol ethers, according to DE-A-37 23 354;

sulfonated unsaturated fatty acids having 12 to 24 carbon atoms and 1 to 6 double bonds, according to DE-A-39 26 344;

esters of tartaric acid and citric acid with alcohols which represent addition products of approximately 2 to 15 molecules of ethylene oxide and/or propylene oxide with fatty alcohols having 8 to 22 carbon atoms.

Preferred anionic surfactants are alkyl sulfates, alkyl polyglycol ether sulfates, and ethercarboxylic acids having 10 to 18 carbon atoms in the alkyl group and up to 12 glycol ether groups in the molecule, and in particular salts of saturated and, in particular, unsaturated C$_8$ to C$_{22}$ carboxylic acids, such as oleic acid, stearic acid, isostearic acid, and palmitic acid.

Nonionic surfactants contain as the hydrophilic group, for example, a polyol group, a polyalkylene glycol ether group, or a combination of polyol and polyglycol ether groups. Such compounds are, for example:

addition products of 2 to 30 mol ethylene oxide and/or 0 to 5 mol propylene oxide with linear fatty alcohols having 8 to 22 carbon atoms, with fatty acids having 12 to 22 carbon atoms, and with alkylphenols having 8 to 15 carbon atoms in the alkyl group;

C$_{12}$ to C$_{22}$ fatty acid mono- and diesters of addition products of 1 to 30 mol ethylene oxide with glycerol;

C$_8$ to C$_{22}$ alkyl mono- and oligoglycosides and their ethoxylated analogs; and addition products of 5 to 60 mol ethylene oxide with castor oil and hardened castor oil.

Preferred nonionic surfactants are alkyl polyglycosides of the general formula R$^1$O—(Z)$_x$. These compounds are characterized by the following parameters:

The alkyl radical R$^1$ contains 6 to 22 carbon atoms and can be both linear and branched. Primary linear radicals, and aliphatic radicals that are methyl-branched at the 2-position, are preferred. Such alkyl radicals are, for example, 1-octyl, 1-decyl, 1-lauryl, 1-myristyl, 1-cetyl, and 1-stearyl. 1-octyl, 1-decyl, 1-lauryl, and 1-myristyl are particularly preferred. When so-called "oxoalcohols" are used as the starting materials, compounds having an odd number of carbon atoms in the alkyl chain predominate.

The alkyl polyglycosides usable according to the present invention can contain, for example, only one specific alkyl radical R$^1$. Usually, however, these compounds are produced from natural fats and oils or mineral oils. In this case the alkyl radicals R that are present are mixtures corresponding to the initial compounds or corresponding to the particular preparation of those compounds.

Those alkyl polyglycosides in which R$^1$ comprises
substantially C$_8$ and C$_{10}$ alkyl groups;
substantially C$_{12}$ and C$_{14}$ alkyl groups;
substantially C$_8$ to C$_{16}$ alkyl groups; or
substantially C$_{12}$ to C$_{16}$ alkyl groups
are particularly preferred.

Any mono- or oligosaccharides can be used as the sugar module Z. Sugars having 5 or 6 carbon atoms, as well as the corresponding oligosaccharides, are usually used. Such sugars are, for example, glucose, fructose, galactose, arabinose, ribose, xylose, lyxose, allose, altrose, mannose, gulose, idose, talose, and sucrose. Preferred sugar modules are glucose, fructose, galactose, arabinose, and sucrose; glucose is particularly preferred.

The alkyl polyglycosides usable according to the present invention contain, on average, 1.1 to 5 sugar units. Alkyl polyglycosides having x values from 1.1 to 1.6 are preferred. Alkyl glycosides in which x is equal to 1.1 to 1.4 are very particularly preferred.

In addition to their surfactant effect, the alkyl glycosides can also serve to improve the fixing of fragrance components on the hair. In the event an effect of the perfume oil on the hair extending beyond the hair treatment period is desired, one skilled in the art will therefore preferably resort to this class of substance as a further ingredient of the preparations according to the present invention.

The alkoxylated homologues of the aforementioned alkyl polyglycosides can also be used according to the present invention. These homologues can contain, on average, up to 10 ethylene oxide and/or propylene oxide units for each alkyl glycoside unit.

Zwitterionic surfactants can additionally be used, in particular as co-surfactants. "Zwitterionic surfactants" refers to those surface-active compounds that carry in the molecule at least one quaternary ammonium group and at least one —COO$^{(-)}$ or —SO$_3^{(-)}$ group. Particularly suitable zwitterionic surfactants are the so-called betaines, such as N-alkyl-N,N-dimethylammonium glycinate, for example, cocalkyldimethylammonium glycinate, N-acylaminopropyl-N,N-dimethylammonium glycinate, for example, cocacylaminopropyl dimethylammonium glycinate, and 2-alkyl-3-carboxymethyl-3-hydroxyethyl imidazoline respectively having 8 to 18 carbon atoms in the alkyl or acyl group, as well as cocacylaminoethylhydroxyethylcarboxymethyl glycinate. A preferred zwitterionic surfactant is the fatty acid amide derivative known by the INCI name cocamidopropyl betaine.

Ampholytic surfactants are also particularly suitable as co-surfactants. "Ampholytic surfactants" are understood to be those surface-active compounds that contain, in addition to a C$_8$ to C$_{18}$ alkyl or acyl group in the molecule, at least one free amino group and at least one —COOH or —SO$_3$H group, and are capable of forming internal salts. Examples of suitable ampholytic surfactants are N-alkyl glycines, N-alkylpropionic acids, N-alkylaminobutyric acids, N-alkyliminodipropionic acids, N-hydroxyethyl-N-alkylamidopropyl glycines, N-alkyl taurines, N-alkyl sarcosines, 2-alkylaminopropionic acids, and alkylaminoacetic acids, having in each case approximately 8 to 18 carbon atoms in the alkyl group. Particularly preferred ampholytic surfactants are N-cocalkylaminopropionate, cocacylaminoethylaminopropionate, and C$_{12-18}$ acyl sarcosine.

The cationic surfactants used in particular according to the present invention are those of the quaternary ammonium compound, esterquat, and amidoamine types.

Preferred quaternary ammonium compounds are ammonium halides, in particular chlorides and bromides, such as alkyltrimethylammonium chlorides, dialkyldimethylammonium chlorides, and trialkylmethylammonium chlorides, e.g., cetyltrimethylammonium chloride, stearyltrimethylammonium chloride, distearyldimethylammonium chloride, lauryldimethylammonium chloride, lauryldimethylbenzylammonium chloride, and tricetylmethylammonium chloride, as well as the imidazolium compounds known by the INCI names quaternium-27 and quaternium-83. The long alkyl chains of the aforementioned surfactants preferably have 10 to 18 carbon atoms.

Esterquats are known substances that contain both at least one ester function and at least one quaternary ammonium group as structural elements. Preferred esterquats are quaternized ester salts of fatty acids with triethanolamine, quaternized ester salts of fatty acids with diethanolalkylamines, and quaternized ester salts of fatty acids with 1,2-dihydroxypropyldialkylamines. Such products are marketed, for example, under the trademarks Stepantex®, Dehyquart®, and Armocare®. Examples of such esterquats are the products Armocare® VGH-70—an N,N-bis(2-palmitoyloxyethyl)dimethylammonium chloride—and Dehyquart® F-75 and Dehyquart® AU-35.

The alkylamidoamines are usually produced by amidation of natural or synthetic fatty acids and fatty acid segments with dialkylaminoamines. One compound from this group of substances that is particularly suitable according to the present invention is the stearamidopropyldimethylamine available commercially under the designation Tegoamid® S 18.

The quaternized protein hydrolysates represent additional cationic surfactants usable according to the present invention.

Also suitable according to the present invention are cationic silicone oils such as, for example, the commercially available products Q2-7224 (manufacturer: Dow Corning; a stabilized trimethylsilylamodimethicone), Dow Corning 929 Emulsion (containing a hydroxyamino-modified silicone that is also referred to as amodimethicone), SM-2059 (manufacturer: General Electric), SLM-55067 (manufacturer: Wacker), and Abil®-Quat 3270 and 3272 (manufacturer: Th. Goldschmidt; diquaternary polydimethylsiloxanes, quaternium-80).

The commercial product Glucquat® 100 (according to INCI nomenclature a "lauryl methyl gluceth-10 hydroxypropyl dimonium chloride") represents one example of a cationic surfactant that can be used.

The respective compounds having alkyl groups that are used as surfactant can be homogeneous substances. It is generally preferred, however, to proceed from native plant or animal raw materials when producing these substances, so that substance mixtures are obtained having different alkyl chain lengths that depend on the particular raw material.

In the case of the surfactants that represent addition products of ethylene oxide or propylene oxide with fatty alcohols, or derivatives of these addition products, both products having a "normal" homologue distribution and those having a restricted homologue distribution can be used. A "normal" homologue distribution is understood as mixtures of homologues that are obtained during the reaction of fatty alcohol and alkylene oxide using alkali metals, alkali metal hydroxides, or alkali metal alcoholates as catalysts. Restricted homologue distributions, on the other hand, are obtained when, for example, hydrotalcites, alkaline-earth metal salts of ethercarboxylic acids, or alkaline-earth metal oxides, hydroxides, or alcoholates are used as catalysts. The use of products having a restricted homologue distribution can be preferred.

The coloring agents according to the present invention can moreover contain further active ingredients, adjuvants, and additives such as, for example:

nonionic polymers such as, for example, vinylpyrrolidone/vinyl acrylate copolymers, polyvinylpyrrolidone, and vinylpyrrolidone/vinyl acetate copolymers, and polysiloxanes;

cationic polymers, such as quaternized cellulose ethers, polysiloxanes having quaternary groups, dimethyldiallylammonium chloride polymers, acrylamide/dimethyldiallylammonium chloride copolymers, dimethylaminoethylmethacrylate/vinylpyrrolidone copolymers quaternized with diethyl sulfate, vinylpyrrolidone/imidazolinium methochloride copolymers, and quaternized polyvinyl alcohol;

zwitterionic and amphoteric polymers such as, for example, acrylamidopropyl/trimethylammonium chloride/acrylate copolymers and octylacrylamide/methyl methacrylate/tert-butylaminoethyl methacrylate/2-hydroxypropyl methacrylate copolymers;

anionic polymers such as, for example, polyacrylic acids, crosslinked polyacrylic acids, vinyl acetate/crotonic acid copolymers, vinylpyrrolidone/vinyl acrylate copolymers, vinyl acetate/butyl maleate/isobornyl acrylate copolymers, methylvinyl ether/maleic acid anhydride copolymers, and acrylic acid/ethyl acrylate/N-tert-butylacrylamide terpolymers;

thickening agents such as agar-agar, guar gum, xanthan gum, gum arabic, karaya gum, locust bean flour, linseed gums, dextrans, cellulose derivatives, e.g. methylcellulose, hydroxyalkylcellulose and carboxymethylcellulose, starch fractions and derivatives such as amylose, amylopectin, and dextrins, clays such as, for example, bentonite or entirely synthetic hydrocolloids such as, for example, polyvinyl alcohol;

structuring agents such as maleic acid and lactic acid;

hair-conditioning compounds such as phospholipids, for example soy lecithin, egg lecithin, and kephalins;

protein hydrolysates, in particular hydrolysates of elastin, collagen, keratin, milk protein, soy protein, and wheat protein, their condensation products with fatty acids, and quaternized protein hydrolysates;

perfume oils, dimethyl isosorbide, and cyclodextrins;

solvents and solubilizers, such as ethanol, isopropanol, ethylene glycol, propylene glycol, glycerol, and diethylene glycol;

fiber-structure-improving active ingredients, in particular mono-, di-, and oligosaccharides such as, for example, glucose, galactose, fructose, fruit sugar, and lactose;

quaternized amines such as methyl-1-alkylamidoethyl-2-alkylimidazolinium methosulfate;

defoamers such as silicones;

dyes for coloring the agent;

anti-dandruff active ingredients, such as piroctone olamine, zinc olamine, and climbazol;

light-protection agents, in particular derivatized benzophenones, cinnamic acid derivatives, and triazines;

substances for adjusting the pH, such as, for example, usual acids, in particular edible acids and bases;

active ingredients such as allantoin, pyrrolidone carboxylic acids, and their salts, as well as bisabolol;

vitamins, provitamins, and vitamin precursors, in particular those of the A, $B_3$, $B_5$, $B_6$, C, E, F, and H groups;

plant extracts such as extracts from green tea, oak bark, nettles, hamamelis, hops, chamomile, burdock root, horsetail, hawthorn, linden blossoms, almonds, aloe vera, pine needles, horse chestnut, sandalwood, juniper, coconut, mango, apricot, lemon, wheat, kiwi fruit, melon, orange, grapefruit, salvia, rosemary, birch, mallow, lady's-smock, wild thyme, yarrow, thyme, lemon balm, restharrow, coltsfoot, hibiscus, meristem, ginseng, and ginger root;

cholesterol;

consistency agents such as sugar esters, polyol esters, or polyol alkyl ethers;

fats and waxes, such as spermaceti, beeswax, montan wax, and paraffins;

fatty acid alkanolamides;

complexing agents such as EDTA, NTA, β-alanine diacetic acid, and phosphonic acids;

swelling and penetrating substances, such as glycerol, propylene glycol monoethyl ether, carbonates, hydrogencarbonates, guanidines, ureas, and primary, secondary, and tertiary phosphates;

opacifiers such as latex, stryrene/PVP copolymers, and styrene/acrylamide copolymers;

luster agents such as ethylene glycol mono- and distearate, as well as PEG-3 distearate;

pigments;

stabilizing agents for hydrogen peroxide and other oxidizing agents;

propellants such as propane/butane mixtures, $N_2O$, dimethyl ether, $CO_2$, and air;

antioxidants.

With respect to further optional components as well as the quantities of those components used, reference is explicitly made to the relevant manuals known to those skilled in the art, for example Kh. Schrader, Grundlagen und Rezepturen der Kosmetika [Cosmetics fundamentals and formulations], 2nd ed. Hüthig Buch Verlag, Heidelberg, 1989.

The agents according to the present invention preferably contain the dye precursor products in a suitable aqueous, alcoholic, or aqueous/alcoholic medium. For hair coloring purposes, such media are, for example, cremes, emulsions, gels, or also surfactant-containing foaming solutions such as, for example, shampoos, foam aerosols, or other preparations that are suitable for application to the hair. It is also conceivable, however, to integrate the dye precursor products into a powdered formulation or even one in tablet form.

Aqueous/alcoholic solutions are understood, for purposes of the present invention, as aqueous solutions containing 3 to 70 wt % of a $C_1$ to $C_4$ alcohol, in particular ethanol or propanol. The agents according to the present invention can additionally contain further organic solvents such as, for example, methoxybutanol, benzyl alcohol, ethyl diglycol, or 1,2-propylene glycol. All water-soluble organic solvents are preferred in this context.

The actual oxidative dyeing of the fibers can be accomplished, in principle, with atmospheric oxygen. It is preferred, however, to use a chemical oxidizing agent, in particular when a lightening effect on human hair is desired in addition to the coloring. Suitable oxidizing agents are persulfates, chlorites, and in particular hydrogen peroxide or its addition products with urea, melamine, and sodium borate. According to the present invention, however, the oxidative color agent can also be applied onto the hair together with a catalyst that activates the oxidation of the dye precursor products, e.g., by way of atmospheric oxygen. Such catalysts are, for example, metal ions, iodides, quinones, or certain enzymes.

Suitable metal ions are, for example, $Zn^{2+}$, $Cu^{2+}$, $Fe^{2+}$, $Fe^{3+}$, $Mn^{2+}$, $Mn^{4+}$, $Li^+$, $Mg^{2+}$, $Ca^{2+}$, and $Al^{3+}$. Particularly suitable in this context are $Zn^{2+}$, $Cu^{2+}$, and $Mn^{2+}$. The metal ions can be used, in principle, in the form of any physiologically compatible salt, or in the form of a complex compound. Preferred salts are the acetates, sulfates, halides, lactates, and tartrates. The use of these metal salts makes it possible both to accelerate coloration and to influence the color tint in controlled fashion Suitable enzymes are, for example, peroxidases that can greatly reinforce the action of small quantities of hydrogen peroxide. Also suitable according to the present invention are those enzymes that directly oxidize the oxidative dye precursor products with the aid of atmospheric oxygen, such as, for example, the laccases; or that generate small quantities of hydrogen peroxide in situ and in that fashion biocatalytically activate oxidation of the dye precursor products. Particularly suitable catalysts for oxidation of the dye precursors are the so-called two-electron oxidoreductases in combination with the substances specific to them, e.g.:

pyranose oxidase and, for example, D-glucose and galactose;

glucose oxidase and D-glucose;

glycerol oxidase and glycerol;

pyruvate oxidase and pyruvic acid or its salts;

alcohol oxidase and alcohol (MeOH, EtOH);

lactate oxidase and lactic acid and its salts;

tyrosinase oxidase and tyrosine;

uricase and uric acid or its salts;

choline oxidase and choline;

amino acid oxidase and amino acids.

The actual hair coloring agent is usefully produced immediately before application, by mixing the oxidizing agent preparation with the preparation containing the dye precursor products. The resulting ready-to-use hair coloring preparation should preferably have a pH in the range from 6 to 12. Utilization of the hair coloring agent in a weakly alkaline medium is particularly preferred. Application temperatures can be in a range between 15 and 40° C. After a contact time of 5 to 45 minutes, the hair coloring agent is removed, by rinsing, from the hair being colored. Subsequent washing with a shampoo is superfluous if a medium having a high surfactant content, e.g., a coloring shampoo, was used.

In particular in the case of hair that is difficult to color, the preparation can applied onto the hair with the dye precursor products but also without prior mixture with the oxidative components. After a contact time of 20 to 30 minutes, the oxidative components are then applied, if applicable after an intervening rinse. After a further contact time of 10 to 20 minutes, a rinse and, if desired, a subsequent shampoo are performed. In this embodiment, according to a first variant in which prior application of the dye precursor products is intended to bring about better penetration into the hair, the corresponding agent is adjusted to a pH of approximately 4 to 7. According to a second variant, firstly an effort is made toward atmospheric oxidation, the applied agent preferably having a pH from 7 to 10. Upon subsequent accelerated post-oxidation, the use of acidic peroxodisulfate solutions as an oxidizing agent may be preferred.

A second subject of the present invention is use of the m-phenylenediamine derivatives according to the present invention for coloring keratinic fibers.

A third subject of the present invention is a method for coloring keratinic fibers in which a hair coloring agent according to the present invention is applied onto the fibers, and rinsed out again after a contact time.

A fourth subject of the present invention are m-phenylenediamine derivatives selected from the group constituted by N-2-(morpholin-4-yl)ethyl-m-phenylenediamine, N-3-(morpholin4-yl)propyl-m-phenylenediamine, and N-3-(imidazol-1-yl)propyl-m-phenylenediamine.

A fifth subject of the present invention are the intermediates in the synthesis of the m-phenylenediamines according to the present invention, selected from the group constituted by N-2-(morpholin-4-yl)ethyl-3-nitroaniline, N-3-(morpholin-4-yl)propyl-3-nitroaniline, and N-3-(imidazol-1-yl)propyl-3-nitroaniline.

The examples below are intended to explain the subject matter of the present invention without, however, limiting it.

Exemplifying Embodiments

1. Syntheses 1.1 N-2-(morpholin-4-yl)ethyl-m-phenylenediamine

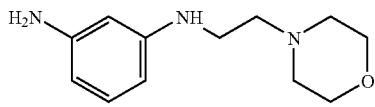

1.1.1 N-2-(morpholin-4-yl)ethyl-3-nitroaniline 28.2 g 3-fluoronitrobenzene and 143 g 4-(2-aminoethyl) morpholine were dissolved in 300 ml dimethyl sulfoxide, and the batch was stirred for 60 h at 100° C. After cooling, the batch was poured into 1 l water. The mixture was extracted several times with methyl tert-butyl ether, and the combined organic phases were reduced to dryness in a rotary evaporator, yielding a dark liquid.

Yield: 20.3 g (40.4%)

1.1.2
N-2-(morpholin-4-yl)ethyl-m-phenylenediamine 20 g N-2-(morpholin4-yl)ethyl-3-nitroaniline was dissolved in 270 ml ethanol and 30 ml water, and 0.3 Pd/C (5%) was added. After purging with nitrogen, hydrogenation was performed for 12 h at 50° C. under 50 bar of hydrogen pressure. After cooling, nitrogen purging was repeated, the catalyst was filtered off, and the filtrate was reduced on a rotary evaporator. 13.2 g of black oil was obtained; this was distilled twice in a ball tube (180–206° C., 0.06–0.08 mbar). The product obtained was a viscous orange oil (middle fraction).

Yield: 4 g (23%)

1.2
N-3-(morpholin-4-yl)propyl-m-phenylenediamine

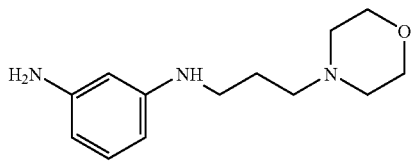

1.2.1 N-3-(morpholin4-yl)propyl-3-nitroaniline 28.2 g 3-fluoronitrobenzene and 158.4 g 4-(3-aminopropyl)morpholine were dissolved in 300 ml dimethyl sulfoxide, and the batch was stirred for 60 h at 100° C. After cooling, the batch was poured into 1 l water. The mixture was extracted several times with methyl tert-butyl ether, and the combined organic phases were reduced to dryness on a rotary evaporator. The product obtained was an orange-brown oil.

Yield: 40.4 g (76.2%)

1.2.2
N-3-(morpholin-4-yl)propyl-m-phenylenediamine 40 g N-3-(morpholin4-yl)propyl-3-nitroaniline was dissolved in 450 ml ethanol and 50 ml water, and 0.5 Pd/C (5%) was added. After purging with nitrogen, hydrogenation was performed for 12 h at 50° C. under 50 bar of hydrogen pressure. After cooling, nitrogen purging was repeated, the catalyst was filtered off, and the filtrate was reduced in a rotary evaporator. 32.2 g of pasty black oil was obtained; this was distilled in a ball tube (220–232° C., 0.06–0.08 mbar). The product obtained was a crystalline orange material.

Yield: 20.4 g (57.8%)

Melting point: 61–65° C.

1.3 N-3-(imidazol-1-yl)propyl-m-phenylenediamine

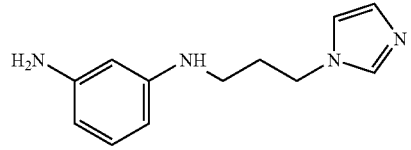

1.3.1 N-3-(imidazol-1-yl)propyl-3-nitroaniline 28.2 g 3-fluoronitrobenzene and 137.5 g 1-(3-aminopropyl)imidazole were dissolved in 300 ml dimethyl sulfoxide, and the batch was stirred for 60 h at 100° C. After cooling, the batch was poured into 1 l water. The precipitated product was suction-filtered and dried overnight under vacuum.

Yield: 28.6 g (58.1%)

Melting point: 135–137° C.

1.3.2
N-3-(imidazol-1-yl)propyl-m-phenylenediamine 28 g N-3-(imidazol-1-yl)propyl-3-nitroaniline was dissolved in 450 ml ethanol and 50 ml water, and 0.3 Pd/C (5%) was added. After purging with nitrogen, hydrogenation was performed for 12 h at 50° C. under 50 bar of hydrogen pressure. After cooling, nitrogen purging was repeated, the catalyst was filtered off, and the filtrate was reduced on a rotary evaporator. 18.2 g of black oil was obtained; this was distilled in a ball tube (265–387° C., 0.06–0.08 mbar). The product obtained was an amorphous orange solid.

Yield: 15.8 g (66.5%)

2. Coloring Tests

2.1 Experimental Protocol

For production of the coloring creme, 50 g of a creme base was weighed into a 250 ml beaker, and melted at 80° C. The creme base used had the following composition:

| | |
|---|---|
| Hydrenol ® D[1] | 17.0 wt % |
| Lorol ® tech. grade[2] | 4.0 wt % |
| Texapon ® NSO[3] | 40.0 wt % |
| Dehyton ® K[4] | 25.0 wt % |
| Eumulgin ® B2[5] | 1.5 wt % |
| Water | 12.5 wt % |

[1] $C_{16-18}$ fatty alcohol (INCI name: cetearyl alcohol) (Cognis)
[2] $C_{12-18}$ fatty alcohol (INCI name: coconut alcohol) (Cognis)
[3] Lauryl ether sulfate, sodium salt (approx. 27.5% active substance; INCI name: sodium laureth sulfate) (Cognis)
[4] N,N-dimethyl-N-($C_{8-18}$ cocamidopropyl)ammonium acetobetaine (approx. 30% active substance; INCI name: aqua (water), cocamidopropyl betaine) (Cognis)
[5] Cetylstearyl alcohol with approx. 20 EO units (INCI name: ceteareth-20) (Cognis)

1/400 mol of each of the developer and coupler components was suspended separately in distilled water and heated to dissolve. Ammonia (<1 ml; 25% ammonia solution) was then added until the pH was between 9 and 10).

The dissolved dye precursor products were successively worked into the hot creme. The volume was then brought up to 97 g with distilled water, and a pH of 9.5 was established with ammonia. After topping up to 100 g with distilled water, the batch was stirred cold (<30° C.), yielding a homogeneous creme.

For the coloring tests, 25 g of each coloring creme was mixed with 25 g of the following oxidizing agent preparation:

| | |
|---|---|
| Dipicolinic acid | 0.10 wt % |
| Sodium pyrophosphate | 0.03 wt % |
| Turpinal ® SL[6] | 1.50 wt % |
| Texapon ® N28[7] | 2.00 wt % |
| Acrysol ® 22[8] | 0.60 wt % |
| Hydrogen peroxide, 50% | 12.00 wt % |
| Sodium hydroxide, 45% | 0.80 wt % |
| Water | to make 100 wt % |

[6] 1-hydroxyethane-1,1-diphosphonic acid (approx. 58–61% active substance; INCI name: etidronic acid, aqua (water)) (Solutia)
[7] Lauryl ether sulfate, sodium salt (min. 26.5% active substance; INCI name: sodium laureth sulfate) (Cognis)
[8] Acrylic polymer (approx. 29.5–30.5% solids in water; INCI name: acrylates/steareth-20 methacrylate copolymer)

A hair strand (80% grayed; wt. 330 mg to 370 mg) was placed into each of the mixtures thus obtained. The mixtures and the hair strands were then each placed on a watch glass, and the hair strands were completely embedded into the coloring cremes. After a contact time of 30 minutes (+/−1 minute) at room temperature, the hair strands were removed and washed with an aqueous Texapon® EVR solution[9] until the excess dye had been removed. The hair strands were dried in air, and their color was determined under a daylight lamp (HE240A color checker) and recorded (Taschenlexikon der Farben [Pocket color dictionary], A. Kornerup and J. H. Wanscher, 3rd unrevised ed. 1981, Muster-Schmidt Verlag; Zürich, Göttingen).

[9] Lauryl ether sulfate sodium salt with special additives (approx. 34 to 37% active substance; INCI name: sodium lauryl sulfate, sodium laureth sulfate, lauramide MIPA, cocamide MEA, glycol stearate, laureth-10)(Cognis)

The results obtained in the coloring tests are listed in the tables below:

2.2 Coloring Tests with N-2-(morpholin-4-yl)ethyl-m-phenylenediamine

| Developer component | Color |
|---|---|
| p-toluylenediamine sulfate | blue-black |
| 2,4,5,6-tetraaminopyrimidine sulfate | olive brown |
| p-aminophenol | ruby gray |
| 4,5-diamino-1-(2-hydroxyethyl)pyrazole sulfate | deep magenta |
| 2-(β-hydroxyethyl)-p-phenylenediamine sulfate | blue-black |
| 4-amino-3-methylphenol | matte violet |
| bis-(2-hydroxy-5-aminophenyl)methane dihydrochloride | gray-brown |

2.3 Coloring Tests with N-3-(morpholin-4-yl)propyl-m-phenylenediamine

| Developer component | Color |
|---|---|
| p-toluylenediamine sulfate | blue-black |
| 2,4,5,6-tetraaminopyrimidine sulfate | dark green |
| p-aminophenol | ruby gray |
| 4,5-diamino-1-(2-hydroxyethyl)pyrazole sulfate | deep magenta |
| 2-(β-hydroxyethyl)-p-phenylenediamine sulfate | lapis blue |
| 4-amino-3-methylphenol | magenta gray |
| bis-(2-hydroxy-5-aminophenyl)methane dihydrochloride | dark ruby |

2.4 Coloring Tests with N-3-(imidazol-1-yl)propyl-m-phenylenediamine

| Developer component | Color |
|---|---|
| p-toluylenediamine sulfate | blue-black |
| 2,4,5,6-tetraaminopyrimidine sulfate | dark green |
| p-aminophenol | dark magenta |
| 4,5-diamino-1-(2-hydroxyethyl)pyrazole sulfate | dark magenta |
| 2-(β-hydroxyethyl)-p-phenylenediamine sulfate | lapis blue |
| 4-amino-3-methylphenol | magenta gray |
| bis-(2-hydroxy-5-aminophenyl)methane dihydrochloride | dark violet |

What is claimed is:

1. An agent for coloring keratinic fibers comprising a cosmetically acceptable carrier and at least one m-phenylenediamine derivative of formula (I)

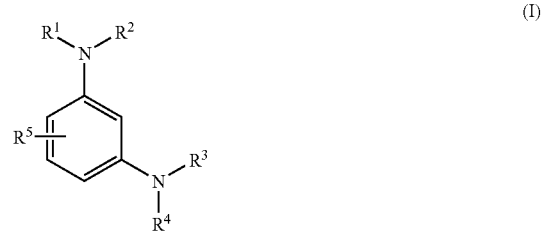

where the radicals $R^1$, $R^2$, $R^3$, and $R^4$ denote, independently of one another, a hydrogen atom, a $C_1$ to $C_4$ alkyl group, a $C_2$ to $C_6$ monohydroxyalkyl group, a $C_3$ to $C_6$ polyhydroxyalkyl group, a $C_1$ to $C_4$ alkoxy($C_1$ to $C_4$) alkyl group, or a radical of formula (II)

—X-Het                                          (II)

where

X denotes a saturated alkylene group having 2 to 6 carbon atoms which optionally can carry one or more substituents selected from: a hydroxy group, a $C_1$ to $C_4$ alkoxy group, or a halogen atom; and Het denotes a 5-, 6-, or 7-member monocyclic, uncharged heterocycle that contains at least one nitrogen atom, one oxygen atom, or one sulfur atom, and optionally can carry up to two substituents other than hydrogen that are selected from: a $C_1$ to $C_4$ alkyl group, a $C_1$ to $C_4$ monohydroxyalkyl group, a $C_1$ to $C_4$ monoaminoalkyl group, a $C_1$ to $C_4$ alkoxy group, a hydroxy group, or an amino group optionally substituted with one or two $C_1$ to $C_4$ alkyl group(s); and R5 denotes a hydrogen atom, a halogen atom, a $C_1$ to $C_4$ alkyl group, a $C_1$ to $C_4$ monohydroxyalkyl group, a $C_2$ to $C_4$ polyhydroxyalkyl group, a $C_1$ to $C_4$ alkoxy($C_1$ to $C_4$ alkyl) group, or a $C_1$ to $C_4$ alkoxy group, with the stipulation that at least one of the radicals $R^1$, $R^2$, $R^3$, or $R^4$ denotes a radical of formula (II), and water-soluble, physiologically compatible salts thereof.

2. An agent according to claim 1, comprising an m-phenylenediamine derivative of formula (I) in which only one of the radicals $R^1$, $R^2$, $R^3$, and $R^4$ denotes a group of formula (II).

3. An agent according to claim 1, comprising an m-phenylenediamine derivative of formula (I) in which the radicals $R^1$, $R^2$, $R^3$, and $R^4$ denote a group of formula (II).

4. An agent according to claim 1, comprising an m-phenylenediamine derivative of formula (I) in which X denotes a propylene group.

5. An agent according to claim 1, comprising an m-phenylenediamine derivative of formula (I) in which the heterocyclic ring system Het contains at least one nitrogen atom.

6. An agent according to claim 1, comprising an m-phenylenediamine derivative of formula (I) in which Het denotes a morpholine4-yl radical or an imidazole-1-yl radical.

7. An agent according to claim 1, comprising an m-phenylenediamine derivative of formula (I) in which $R^5$ denotes a hydrogen atom.

8. An agent according to claim 1, comprising an m-phenylenediamine of formula (I) selected from the group consisting of N-2-(morpholine-4-yl)ethyl-m-phenylenediamine, N-3-(morpholine-4-yl)propyl-m-phenylenediamine, and N-3-(imidazole-1-yl)-propyl-m-phenylenediamine and water-soluble, physiologically compatible salts thereof.

9. An agent according to claim 1, additionally comprising at least one developer component.

10. An agent according to claim 1, additionally comprising at least one further coupler component.

11. An agent according to claim 1, additionally comprising at least one direct-absorbing dye.

12. An agent according to claim 11, wherein the direct-absorbing dye is cationic.

13. An agent according to claim 1, wherein Het denotes a furanyl radical, a pyrrolyl radical, a pyrrolidinyl radical, a piperidinyl radical, a pyrazolyl radical, an oxazolyl radical, a triazolyl radical, a morpholinyl radical, an imidazolyl radical, a thiazolyl radical, an isoxazolyl radical, an isothiazolyl radical, or a piperazinyl radical.

14. An agent according to claim 1, wherein X denotes an ethylene group or a propylene group.

15. An agent according to claim 1, wherein one of the two radicals $R^1$ and $R^2$ and one of the two radicals $R^3$ and $R^4$ denote a group of formula (II).

16. A method for coloring keratinic fibers comprising applying an agent according to claim 1 onto the fibers and rinsing said agent off after a contact time.

* * * * *